US009683208B2

(12) United States Patent
Stadler (10) Patent No.: US 9,683,208 B2
(45) Date of Patent: Jun. 20, 2017

(54) HORIZONTAL SINGLE USE PRESSURIZABLE MODULAR MULTI-AGITATOR MICROBIAL FERMENTATOR

(71) Applicant: Ernest Louis Stadler, Nazareth, PA (US)

(72) Inventor: Ernest Louis Stadler, Nazareth, PA (US)

( * ) Notice: Subject to any disclaimer, the term of this patent is extended or adjusted under 35 U.S.C. 154(b) by 0 days.

(21) Appl. No.: 15/218,136

(22) Filed: Jul. 25, 2016

(65) Prior Publication Data

US 2017/0029758 A1    Feb. 2, 2017

Related U.S. Application Data

(60) Provisional application No. 62/282,404, filed on Jul. 31, 2015.

(51) Int. Cl.
| | | |
|---|---|---|
| *C12M 1/00* | (2006.01) | |
| *C12M 3/00* | (2006.01) | |
| *C12M 1/06* | (2006.01) | |
| *C12M 1/02* | (2006.01) | |

(52) U.S. Cl.
CPC ............ *C12M 23/14* (2013.01); *C12M 23/28* (2013.01); *C12M 23/44* (2013.01); *C12M 27/00* (2013.01); *C12M 27/02* (2013.01); *C12M 27/20* (2013.01); *C12M 41/24* (2013.01)

(58) Field of Classification Search
CPC ....................................................... C12P 19/04

USPC ................................. 435/289.1, 290.2, 298.1
See application file for complete search history.

(56) References Cited

U.S. PATENT DOCUMENTS

| | | | | |
|---|---|---|---|---|
| 3,853,712 | A * | 12/1974 | House ..................... | C12M 27/20 435/293.2 |
| 4,962,033 | A * | 10/1990 | Serkes ..................... | C12M 23/08 435/298.2 |
| 7,491,324 | B2 * | 2/2009 | Moulton .................... | C02F 1/74 210/150 |
| 8,158,426 | B2 * | 4/2012 | Wilson .................... | C12M 23/08 435/297.1 |
| 8,551,740 | B2 * | 10/2013 | Hsiao ....................... | C12P 19/04 435/101 |
| 2010/0317066 | A1 * | 12/2010 | Hsiao ....................... | C12P 19/04 435/101 |

(Continued)

*Primary Examiner* — Nina Bhat (57) ABSTRACT

A scalable horizontal single-use pressurizable modular multi-agitated portable fermentor for culturing microorganisms to high cell density with high oxygen mass transfer capability is provided. The fermentor is suitable for laboratory use, process development suites and large scale production facilities. The disposable sterile bag, constructed of thin polymer film, incorporates a single-use magnetically driven turbine impeller. The single-use bag is fully contained in a stainless steel bag retention vessel designed to permit the bag to be pressurized. Conventional fermentor control is used to facilitate oxygen mass transfer rates suitable for optimal microbial growth, metabolism, and recombinant protein product formation. Horizontal modules, each having an independent agitator, enables scaling-out while maintaining constant input power per unit volume. Increasing the bag retention vessel/bag diameter enables scaling-up to large batch sizes. Alternate impeller types are provided for high gas flow when needed to support high cell density cultures.

25 Claims, 5 Drawing Sheets

Base Unit (56) References Cited

U.S. PATENT DOCUMENTS

2012/0252105 A1* 10/2012 Ahrens ................ C12M 21/02
435/257.3

* cited by examiner

FIG 1

Base Unit

FIG 2

Dual Module Unit

FIG 3

Triple Module Unit

FIG 4

Magnetic Drive Assembly

FIG 5

Curved Blade Turbine Impeller with Vortex Generators and Scalloped Lower Blades

HORIZONTAL SINGLE USE PRESSURIZABLE MODULAR MULTI-AGITATOR MICROBIAL FERMENTATOR

1. FIELD OF THE INVENTION

This invention relates to the field of microbial fermentation for production of recombinant therapeutic proteins. In particular, this invention provides a scalable disposable culture bag for use in both non-GMP (Good Manufacturing Practice) R&D environments as well as cGMP (current Good Manufacturing Practice) production facilities making FDA licensed biopharmaceutical proteins.

2. BACKGROUND OF THE INVENTION

Current single use (SU) small and large scale cell culture bioreactors used for development work in pilot plants or for full scale GMP production are typically designed with a vertical vessel that holds a disposable bag fully instrumented and with necessary gas flows and sterile inlet and outlet filters. In addition, many SU cell culture bioreactor mixer designs are limited in the power they are able to deliver into the culture fluid. The industry has been seeking to provide a single use microbial fermentor by leveraging what has been learned from the single use cell culture bioreactors on the market. Some single use vertical microbial fermentors have been introduced with a single drive shaft having multiple impellers. Single vertical shaft designs also utilize complicated internal shaft support bearings to stabilize the rotor. Magnetic drives that avoid dual mechanical shaft seals through the pre-sterilized bag are preferred. However the nature of the magnetic coupling that occurs limits the mixing power delivered to the fluid as compared to an equivalent stainless system using direct shaft drives having dual mechanical shaft seals.

Some current vertical single use fermentor designs have mixing limitations with respect to impeller tip speeds and shaft rotational speed and stability, particularly when the available impeller limitations might result in long mixing times, poor oxygen mass transfer, or restrictions on minimum operating level in the bag. Single use cell culture bioreactor systems have gained great success in mammalian cell applications (as an example culturing chinese hamster ovary (CHO) cells) to produce monoclonal antibodies (MaB's) where low power per unit volume and long mixing times are tolerable due to the slow metabolism of the cells. Cell culture bioreactors typically have batch runs of 21 to 30 days with relatively gentle mixing with low gas flows even during the maximum cell density stage where product formation occurs.

Vertical single use bags are being developed for microbial fermentation applications to varying degrees of success however there remains the challenge of delivering high power per unit volume and high oxygen transfer rates, particularly for the magnetic drive solutions. In addition these vertical form factor vessel systems at large scale (>1000 liters working volume) require significant accommodations for operator access to the top of the bag for installation and removal of the bag, the inlet and exhaust filters, and possible other components such as sensors and exhaust condensers at the top bag gas outlet. In very large systems at 1500 liter scale or greater, some facility consideration must be made for high ceiling stub-ups (greater than 9 ft.), mezzanines or permanent platforms to permit safe operator access.

There is a market need for a scalable single use microbial fermentor solution that is capable of delivering the necessary power per unit volume input, sparge air flows of 1 vessel volume per minute (VVM) or higher, optional sparge oxygen flow of 1 VVM, a pressurized environment and effective mixing times with attendant aggressive agitation to support the high oxygen mass transfer rate needed for microbial growth kinetics and metabolism of pharmaceutical recombinant therapeutic proteins, vaccines and other fermented products. In addition to the vertical single use cell culture bioreactors currently in use, other types of bioreactors such as rocker plate, rocker plus translation motion, orbital shaker, air lift/air wheel, packed bed, or other novel designs also have the inability to achieve high power per unit volume input to the liquid thereby making them ineffective for efficient fast microbial growth while they are quite satisfactory for slow growing mammalian cell cultures.

Current polymer bioreactor and fermentor bag holder designs with an open top container limit operating pressures to about 0.5 psig to prevent bag bursting that could cause injury to personnel and/or release of valuable and/or cytotoxic material to the environment. This low operating pressure, while not of consequence in cell culture bioreactors, does restrict oxygen mass transfer capability in microbial fermentations. Equivalent stainless steel fermentor systems can have relatively high operating pressures of typically 10 to 15 psig that contribute to driving force and high oxygen mass transfer required at relatively high cell densities thereby aiding metabolism.

Current vertical tank bag holders are conducive to single bottom or top mixer drives often with magnetic coupling to avoid breaching the bag boundary with a mechanical seal. The magnetic flux coupling between the drive magnets and the driven magnets limits torque transmission which in turn limits top speed, impeller tip speed, oxygen mass transfer, and number of impellers permitted on a given shaft. Typically as working volume increases to 500 liters and beyond, multiple impellers are needed to avoid stratification and these extended length shafts do not operate well at high speeds with a bottom or top magnetically coupled drive. In the case of top drives, multiple impellers are possible but vibration and critical speed issues due to longer shafts as well as power per unit volume input and top speed limitations makes them unsuitable for high cell density microbial fermentations.

Current large scale SU vertical bioreactors (1000 L and greater) are not conducive to use in modular clean room facilities where ceiling height limitations (typically 9 ft.) make scale-up more difficult. Vertical bag holders can easily exceed the 9 foot ceiling limitation of a typical modular building thus making special ceiling "top hats" or "stub-ups" necessary. This complicates the design and construction of modular facilities. Further, large scale, 1000 liter working volume and larger vertical SU bioreactor or fermentor designs are not portable or modular thus tending to remain fixed in place once the bioreactor suite is installed.

Current market drivers for single use technology in biopharmaceutical manufacture are: improved speed of production thus faster time to market, flexibility of equipment to easily adapt to process changes, avoidance of cleaning and steam sterilization, as well as a reduction in capital cost. Classic stainless steel multi-use microbial fermentors and mammalian cell culture bioreactors have been used in the Pharmaceutical and Biotechnology industries for over 40 years. Many drug production companies have FDA validated processes thus their existing infrastructure and stainless steel equipment remain their dominant and/or preferred design.

The market for SU cell culture bioreactors at lab, process development and even large production scale has and will continue to grow as these designs prove to meet the demands of the industry. Mammalian cells and other eucaryotic cells continue to dominate the expression systems needed to produce large quantities of monoclonal antibodies and biotherapeutic proteins.

By contrast current microbial fermentors in the single use market have limitations inherent in their design ranging from use of unpressurized or very low pressure disposable bags and magnetic drives that do not achieve equivalent mixing and mass transfer of oxygen as their stainless steel counterparts can deliver.

Some vertical form factor fermentors are on the market up to 300 liters working volume that claim adequate mixing and oxygen mass transfer to achieve successful microbial growth and product formation. Newly released 1000 L single use fermentors are being introduced however there is very little in the way of actual production use to date. Microbial cells can be nurtured and grown to produce relatively high density cell mass. This cell mass then can produce high titers of metabolites (products of cell metabolism) or produce proteins when the cells have been genetically engineered to produce large quantities of a specific recombinant protein. Large product quantity requires the use of large scalable fermentors in the 1000 liter to 3000 liter working volume range. Current single use microbial fermentors cannot scale to this size leaving a void in the production capacity of these systems.

The products made in this type of equipment range from perfume, fuel, and amino acids to a wide array of vaccines, therapeutic recombinant proteins, monoclonal antibodies, and various sophisticated fusion proteins or other polypeptides.

The fermentor systems whether they are stainless steel or single use require instruments, piping components, manual and automatic valves, gas flow control, agitators for mixing and oxygen mass transfer, temperature control modules, pressure control, liquid addition and harvest systems, overpressure safety systems, and a range of digital controllers properly configured to monitor and control the microbial process successfully. Successful operation is defined as controlled metabolism of the organism during cell doubling followed by proper production or expression of the product of interest. The current single use systems needed to efficiently grow and metabolize mammalian cells have copied from stainless steel vertical bioreactor vessels having a single agitator with one or several impellers coupled to a single shaft drive system.

Attempts are being made to create single use microbial fermentors using previously mentioned rocker plates, orbiting shakers, airlift wheels, paddle mixing and other novel designs, none of which are capable of achieving the necessary scalability in terms of input power per unit volume. The current vertical fermentor single use systems have limited power per unit volume capability upon scale-up result in inadequate mixing and oxygen mass transfer particularly since they are non-pressurized systems. In addition larger size single use systems result in very tall vessels that require special considerations when fitting into clean rooms, modular construction buildings or other portable type production facilities. Use of ladders, platforms, or other super-structures complicate access to the fermentor and may add to operator turn-around time between batches.

In addition the current vertical form factor for single use fermentors prohibits the possibility of portability that is a prerequisite for rapid deployment when a therapeutic recombinant protein or vaccine is needed in a fast time frame as an example, medical counter measures (MCM) in the event of a biological toxin release.

Further, culture of microorganisms in single use bags creates a conundrum since said microorganisms are grouped in various biosafety levels for large scale production (greater than 10 liter batches). The National Institutes of Health (NIH) specifies physical containment levels and defines Biosafety Levels for Large Scale in their "Guidelines for Research Involving Recombinant DNA Molecules" (NIH Guidelines)—Appendix K—"Physical Containment for Large Scale Uses of Organisms Containing Recombinant DNA Molecules". April 2002. These categories range from safest to most hazardous in the following categories, Good Large Scale Practice (GLSP), BL1-LS, BL2-LS, and BL3-LS. These categories closely match the Center for Disease Control (CDC) categories but the CDC also includes a fourth category, BSL4 however these types of cultures are not recommended for use in any type of bag or single use container due to their inherent hazard to human exposure.

Current single use disposable fermentors have not addressed any type of secondary containment in situations where BL2-LS and/or BL3-LS organisms may be needed for production purposes.

3. SUMMARY OF THE INVENTION

The present invention provides an apparatus and system for culturing microorganisms that utilizes a low profile horizontal single use and pressurizable bag retention vessel. The bag is fully captive within the bag retention vessel and yet fully accessible for bag deployment via a sealed top access port and a full swing open and sealable dished head having quick release clamps. The heads and horizontal cylindrical body of the bag retention vessel has dimpled heat transfer surface (HTS) area and stainless steel HTS covers to facilitate precise temperature control of the culture via an external connected temperature control module (TCM).

According to one aspect of the invention, the bag retention vessel will serve as a secondary seal by sealing the bag at all points where the bag or agitator penetrate the bag retention vessel. A leak detector will be incorporated to sense any moisture that accumulates at the low point between the bag exterior and the bag retention vessel interior surface. An alarm set off by the leak detector will shut off any air/gas flow thereby reducing the internal bag pressure to zero. The agitation will also be shutdown as well as isolating the inlet sparge gas and exhaust gas lines. Further operator actions may then take place to allow them to dealing with containment safely.

The new invention combines all necessary mechanical and automation systems necessary for microbial growth and final recombinant protein production into a modular horizontal vessel format SU bag design. Upon modular scale-out this horizontal design will utilize multiple agitators to maintain constant power per unit volume ratio for optimizing microbial growth. The range of sizes will cover small and large scale production up to and possibly beyond 3000 liters working volume. The pressurizable modular horizontal format bag holder will permit high P/V (power per unit volume) across the range of sizes as well as higher operating pressures (5 psig) than current non-pressurizable vertical large scale bag designs which are limited to about 0.5 psig operation.

4. BRIEF DESCRIPTION OF THE DRAWINGS

FIG. 1 is an transparent elevation view of a horizontal pressurizable modular single use microbial fermentor. The primary component that captures the single use bag is the bag retention vessel (BRV) 10. The top access port (not shown), swing open access dished head 12 with quick action clamps 14, magnetic drive agitator 16, baffles 20, and agitator mounting plate 16 are identified.

FIG. 2 is a transparent elevation of the base unit and one (1) expansion module 22 shown via a transparent view of the bag retention vessel (BRV) 10 for clarity. The addition of an expansion module 22 and second agitator 16 will double operating capacity over the base unit capacity. The sterile dual module SU bag 26 is indicated by arrow to internal cavity of the BRV. The six (6) baffles 20 shown are for the purpose of enhancing mixing and oxygen mass transfer from the magnetic drive agitator 24. In this configuration the swing open access dished head 12 has been relocated to the new position to accommodate the increased working volume.

FIG. 4 is an exterior view of the hermetically sealed sterile magnetic drive multi-use agitator with removable and interchangeable impellers. The impeller 40 is secured by a sanitary and removable connection to the rotating driven magnet housing 42 which in turn captures the outer race of the ball bearing 44 (not shown). The stationary inner race of the ball bearing is captured by the bearing support post 46. The bearing support post 46, the sparge plate 48, the bag mounting plate 50, and the clamping plate (not shown) form a removable assembly held together with bolts and sealed for sanitary application with multiple o-rings 58. The bag film 56 is heat sealed to the bag mounting plate 50 to form an integral part of the SU bag.

5. DETAILED DESCRIPTION OF THE PREFERRED EMBODIMENTS

Considering the drawings illustrated in FIG. 1 through FIG. 5, a modular pressurizable single use microbial fermentor with expansion modules, baffled bag retention vessel, sterile single use bag, and multiple agitators is illustrated. The bag retention vessel (BRV) 10 is structural and preferably made of stainless steel to include a horizontally oriented cylindrical shell, a welded dished head on one end and a swing open and removable dished head on the opposite end. The BRV is supported on load cells and mounted on a portable frame that will support all systems necessary to properly operate the fermentor in culturing procaryotic microbial cells. The BRV has access space at the bottom for mounting of a magnetic drive agitator complete with retractable mechanism for insertion and removal of the drive magnets from the drive post 46 cavity. The fixed head will have access for all sensors, fluid and gas inlets/outlets while the swing open head will remain unencumbered to facilitate reuse when expansion modules are inserted into the horizontal cylinder. The swing open head serves to facilitate removal of a used bag and for deployment of new sterile SU fermentation bag. The top access port 18 also facilitates deployment of new pre-sterilized SU fermentation bags giving operators the ability to correctly position the bag over the internal BRV baffles. The BRV is designed to completely contain the bag thereby allowing pressurization to 5 psig to enhance input power per unit volume and driving force for oxygen transfer rate (OTR) greater than 200 mMoleOxygen per Liter per Hour using air only sparge (no oxygen enrichment) conventional Rushton Turbine impellers. Higher OTR's are possible when using oxygen sparge gas enrichment, the proprietary curved blade impeller with vortex generators and scalloped bottom blades where sparge gas enters the impeller blade area under the impeller disk.

Figure 1:
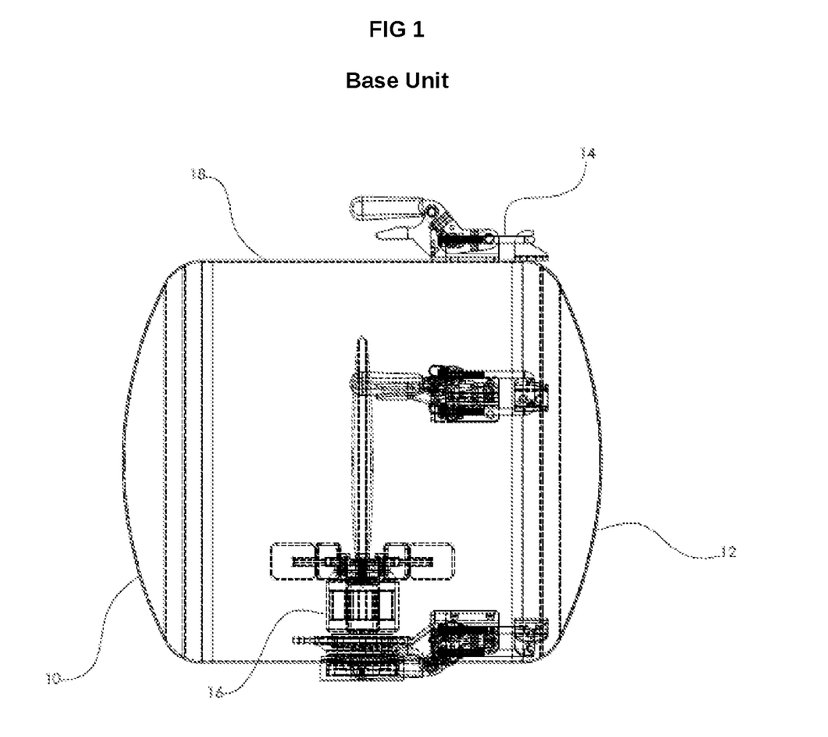

The fermentation fluid containment bag is of thin wall film and therefore has no structural integrity. The complete BRV 10 enclosure may also be sealed via o-rings to provide a secondary barrier for containment any fluid that may leak out of the primary SU fermentation bag. In this event, a leak sensor will also be employed to alert the operators of a possible breach of the primary containment bag.

Figure 2:
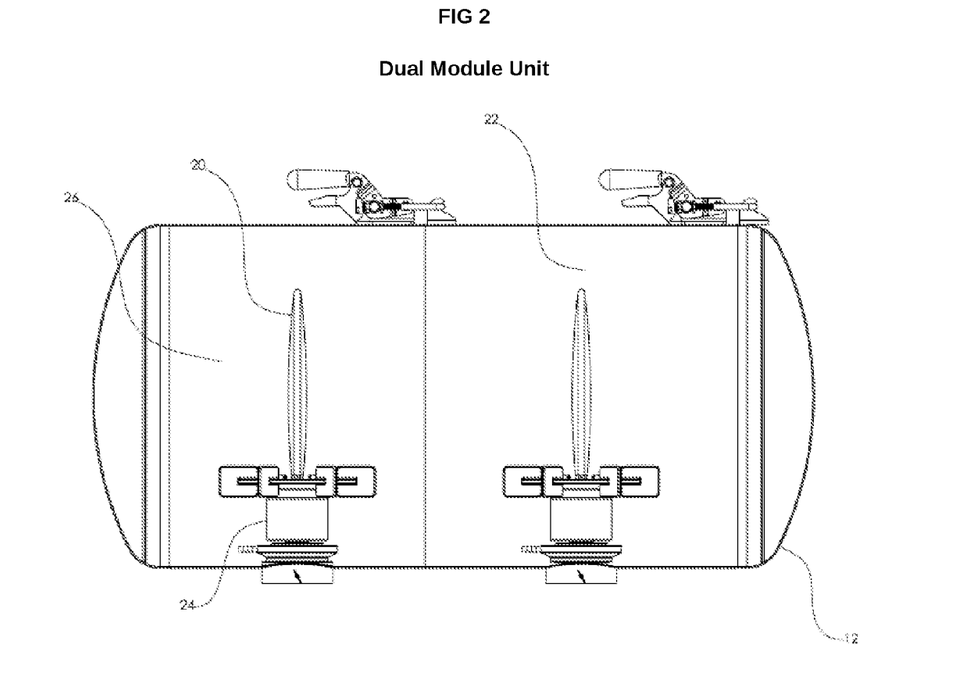

Bag 26 deployment consists of engaging the bag assembly clamping plate 52 into the recess of the agitator support plate 54 and aligning the bag baffle sleeves over top of the BRV baffles 20. Sterile sparge air is introduced to the bag to begin inflation while the operator continues to move and position the bag around the baffles. Once the bag is partially inflated, the swing open dished head 12 is closed and clamped shut. Inflation then continues while the operator has access by the top head port 18 to continue to align the bag properly by engaging the bag baffle sleeves with the baffles 20. The top head port (not shown) is equipped with a close fitting plug that contours to the radius of the bag and it is inserted and fastened into place upon completion of bag inflation and prior to filling of any sterile fluid such as growth media.

The BRV 10 and swing open dished head 12 are equipped with integral heat transfer channels on the outside to provide for temperature control of the fermentation through the use of an external and independent temperature control unit (TCU). The BRV 10 integral cooling/heating channels include movement of cooling fluids separately through the baffles 20 which are fully seal welded to the inside surfaces of the cylindrical shell and dished heads that make up the complete BRV 10. Flow of heating and cooling fluid to the BRV is controlled by external flexible tubing and multiple connection points for supply and return to balance all flows for uniformity of temperature control of the fermentation broth.

Figure 4:
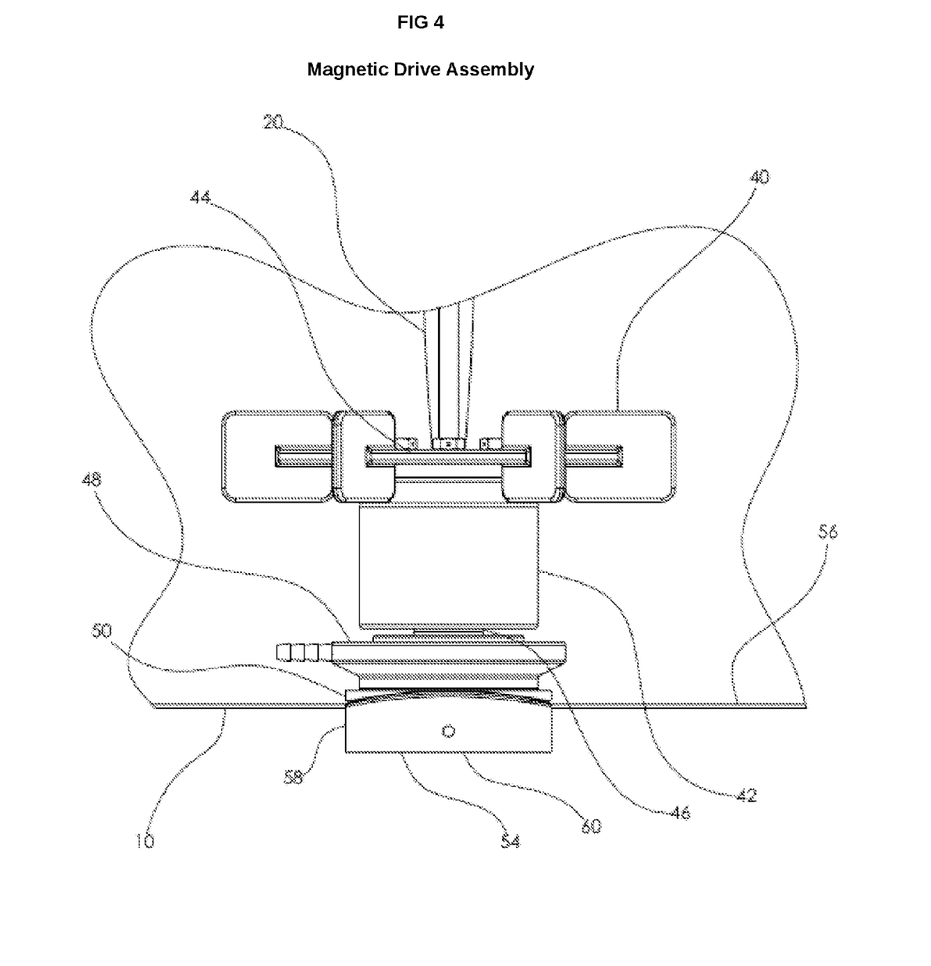

All fluid and gas introduced to or removed from the fermentation broth is routed through flexible sanitary tubes with sanitary SU connectors directly integral with the bag 26. Sparge gas and exhaust gas are directed through external sterile filters connected by sanitary SU connections to the respective tubes on the bag. Media, Inoculum, and nutrient additions as well as acid/base/antifoam for controlling pH and foam level are also introduced via tubes integral with the bag 26 and will usually be seal welded shut until installation and sterile connection to external control devices. Sensors for pH, DO (dissolved oxygen), temperature, foam level, pressure are all connected to the bag 26 using traditional sanitary design to preserve sterility. All fluid and gas supply/return and sensors are handled through the fixed head welded integral to the BRV 10. Upon completion of the batch fermentation process, harvesting culture fluid from the bag is accomplished by draining from the sparge gas line through the sparge plate 48.

The agitation apparatus includes a turbine impeller 40 supported on a double row ceramic ball bearing 44 (not shown) that is supported by a fixed bearing support post 46. The preferred embodiment is that the impeller and several parts comprising the complete agitator are reuseable when properly decontaminated and cleaned before reuse in a new bag. This reuseable component of the design is to conserve valuable material such as rare earth magnets as well as reducing waste material that must be recycled or disposed of. Single use polymer parts may be subjected to a limited number of reuse cycles as a result of degradation of polymer cross-linking from multiple gamma radiation sterilization cycles. Other parts may be manufactured of stainless steel assuring multiple reuse cycles with no sensitivity to gamma radiation degradation. The driven magnets are encased in either a stainless steel housing for complete reuse or in a sealed polymer housing manufactured by AM3D printing. The drive magnets are of a standard design from a $3^{rd}$ party supplier and fit into the cavity formed after assembly of the bearing support post 46, the sparge plate 48, the bag and heat sealed mounting plate 50, and the clamping plate 52 all held together with sealing o-rings and bolts to form a completely sanitary and reuseable assembly. The clamping plate (not shown) is positioned and held in place by spring loaded retractable position pins mounted in the agitator support plate 54. The position pins are engaged as the first step upon positioning of the bag during deployment.

Agitation can be characterized by energy dissipation in watts per kilogram of liquid mixed and typical agitation is in the Modest (above 0.2 watts per kilogram) to Vigorous (above 1.0 watts per kilogram) mixing regime. When the energy dissipation is 3 watts per kilogram or higher, it can be characterized as Severe and this type of agitation is reserved for only the most aggressive fermentation batches using cells with very high power per unit volume input to metabolize and grow properly. This agitation system with magnetic drive is designed to deliver in excess of 3 watts per kilogram characterizing the mixing as well above Vigorous and into the Severe range of energy dissipation. This is fundamentally necessary particularly upon scale up to large volume SU fermentors to assure optimal microbial growth and metabolism. The concept of modular expansion with additional agitators will assure a constant power density in watts/L and energy dissipation in watts/Kg as any fermentation process is scaled up from the smallest 50 L size to the largest 3000 L working volume size.

Mixing power density is only one driving force for assuring high oxygen mass transfer in microbial fermentations. Another consideration is using pressure as a driver for increasing oxygen mass transfer. The BRV and bag are designed to withstand a minimum of 5 psig internal pressure. Each increase of 5 psig above atmospheric pressure will increase oxygen driving force by 33%. No current SU bag bioreactors or fermentors on the market are capable of operating under pressure. Typical oxygen mass transfer rates in stainless steel SIP and CIP fermentors is in the range of 150 to 200 mMoleOxygen/Liter/hr (air only sparge, no oxygen enrichment). An additional consideration to enhance oxygen driving force is the ability to sparge sufficient quantities of air and/or mix of air/oxygen into the vessel. The sparge tube and sparge plate 46 are designed to input 1 VVM (vessel volume per minute) of air into the broth. In addition the control system will be capable of delivering 1 VVM of oxygen gas as well. The combination of air and oxygen mass flow controllers will enable oxygen transfer rates in excess of 200 mMoleOxygen/Liter/Hr using various mixing proportions of air to gas through out the fermentation for optimizing the growth and metabolism of the organism. Gas is delivered by the sparge plate 46 through orifice holes directed towards the underside of the impeller disk. This optimal location enables the impeller 40 to effectively disperse the gas as numerous small bubbles making the oxygen more available in terms of the ratio of bubble surface area to broth volume. The better the bubble dispersion, the higher will be the ability to dissolved the gas into the liquid where the oxygen may be available for uptake by the cultured organism. This can be measured as Kla (coefficient of oxygen mass transfer) for any given geometry and agitation system. The horizontal cylindrical design lends itself to a relative low liquid level whereby the single impeller of substantial size, tip speed, and power input per unit volume may achieve a relatively high coefficient of mass transfer (Kla). The baffles 20 further impart substantial mixing by encouraging secondary flow patterns that superimpose vertical top to bottom mixing over the radial mixing flow pattern initiated by the radial flat or curved turbine impeller blades. Key to achieving excellent microbial growth upon scale-out and scale-up is the implementation of multiple agitators when volume is increased by installing expansion modules. Scaling up to larger diameter cylinders implies scaling up the impeller to vessel and baffle geometry in such a way that impeller tip speeds remain fairly constant and the power input in horsepower (HP) per unit volume is maintained as constant. Microbial productivity for expression of proteins of interest at 50 Liter scale will be identical to productivity at 3000 Liter scale.

Figure 5:
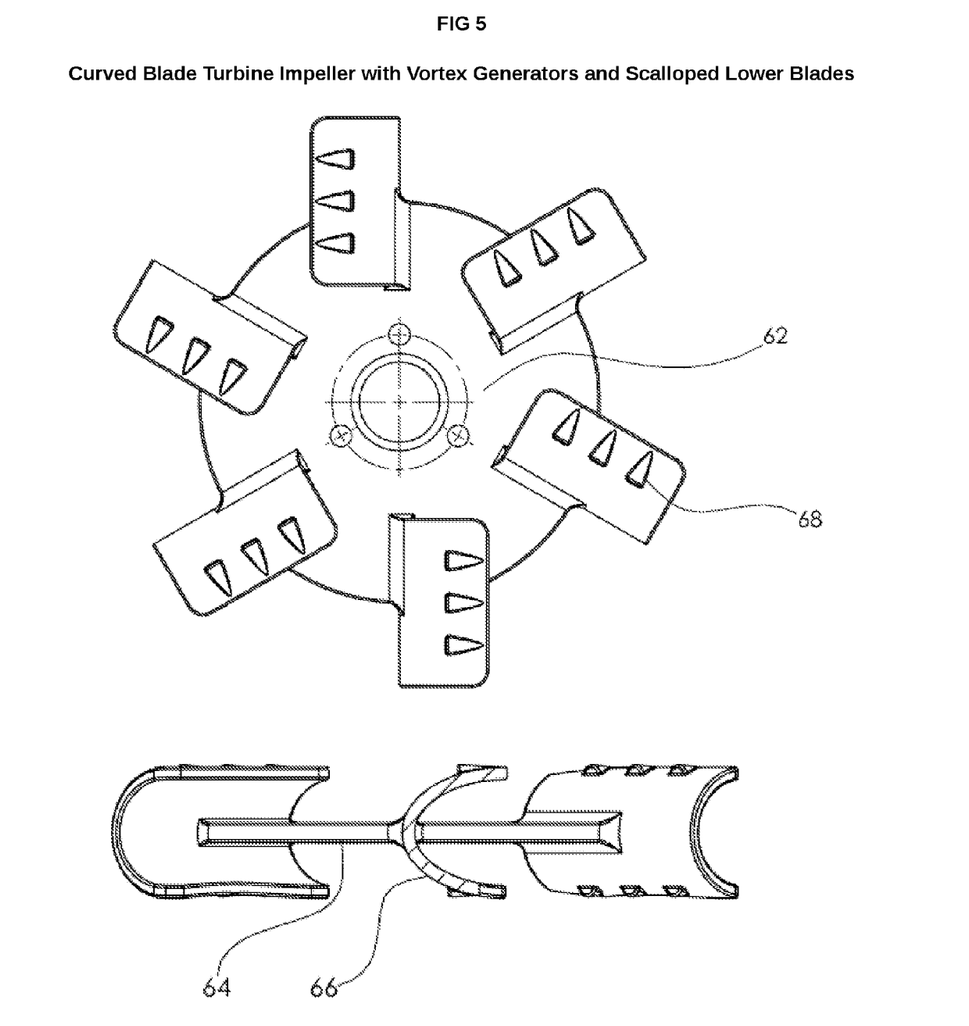
FIG. 5 is a representation of the high gas flow custom curved turbine blade impeller with sparge air scallop cutouts in lower blade surfaces and vortex generators on top and bottom blade surfaces. The hub 62 mounts on the bearing support post 46 and ball bearing 44 and it is integral with the disk 64 and blades 66. The vortex generators 68 are also integral with the blades and are formed on the top and bottom blade surface of each individual blade.

A basic standard design Rushton Turbine Impeller 40 will typically provide very substantial agitation for optimal growth, metabolism and product formation. The standard Rushton Turbine is defined as an impeller with the ratio of 20:5:4 where 20 is the OD (outside diameter), 5 is the blade width, 4 is the blade height and the disk has a diameter of 20−5=15 and these may be units of inches or cm. An alternate impeller having curved blades 66 equipped with vortex generators will provide advantages where very high aeration is needed to support oxygen transfer rates in excess of 300 mMole Oxygen/Liter/hr and when oxygen enriched gas is sparged into the bag. The vortex generators encourage additional mixing vortexes coming off the top and bottom blade surfaces to further disperse oxygen bubbles into the broth rather than relying on only blade shear along the trailing edges and at the tip. The blades 66 are uniquely designed with a proprietary compound radius and the lower blades are scalloped to permit the sparge gas to enter the blade cavity where gas dispersion takes place.

Figure 3:
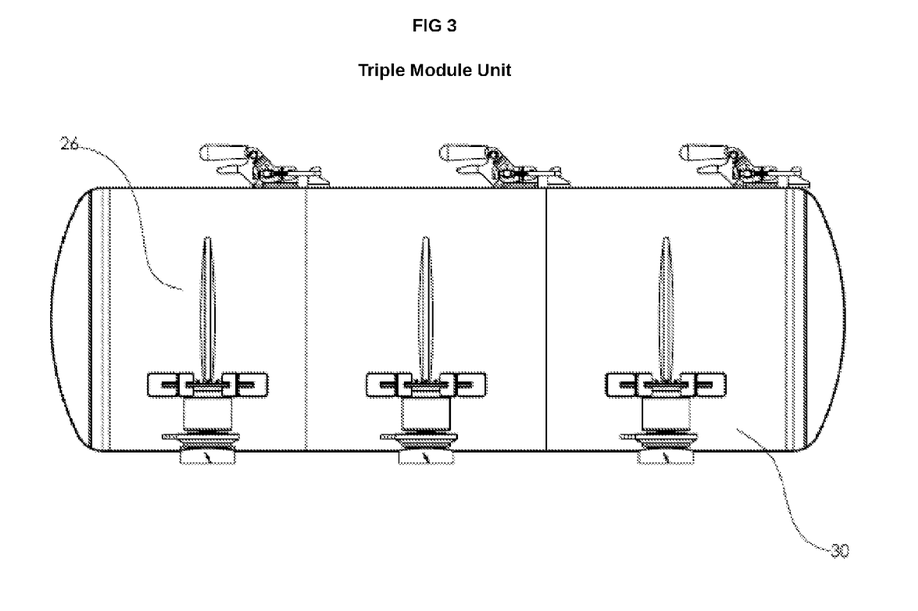
FIG. 3 is a transparent elevation view of a three (3) module expanded SU fermentor 30. Scale out is accomplished by the addition of two (2) expansion modules 22 and two (2) additional agitators 24 to increase operating capacity by triple over the base unit. The sterile triple module SU bag 26 is indicated by arrow to internal cavity of the expanded BRV.

A further unique result from the use of dual or triple agitators as modular expansion units are installed to increase capacity is the infinite combination of mixing speeds and mixing rotational direction that the individual agitator controllers can provide. For example, with two agitators and a dual module unit and bag, the impellers may operate at different speeds and in similar or opposite rotation direction both of which may be useful for developing high yield fermentation batches. Current designs utilizing a single agitation shaft with one or more impellers are locked into a fairly inflexible mixing paradigm. In the example of a triple agitation unit with the base BRV and two expansion modules, the three (3) impellers may all operate at different speeds and any combination of rotation direction that established optimal growth conditions for the batch. This variability will be particularly useful in an R&D setting where processes are constantly being analyzed for process intensification, i.e. doing more with less.

Thus, a horizontal pressurizable modular single use high performance microbial fermentor is disclosed. While embodiments and applications of this invention have been shown and described, it will be apparent to those knowledgeable in the art that the form factor, agitation, aeration, pressurization, gas dispersion, input power per unit volume, and impeller tip speeds as well as impeller configuration are in concert able to permit a single use solution for microbial fermentations that will perform similar to historically designed stainless steel fermentors which have been designed for steam in place (SIP) and clean in place (CIP). In addition the form factor of a horizontal design at the 3000 L scale is highly conducive to installation in low ceiling height clean room facility particularly where a rapid deployment of a process is needed to produce vaccines or therapeutic proteins very quickly. Details of these claims are further described as follows:

What is claimed is:

1. A horizontal fermentor for production of microbes comprising:
    a horizontal disposed cylindrical vessel wherein:
    said vessel is oriented so that the axis of the cylinder is horizontal; said fermentor comprising includes:
        a first head affixed to and sealing the first end of the cylinder; and
    a second head affixed to a second end of the cylinder, the second head operable to open allowing access to the interior of the cylinder and operable to close thereby sealing the second end of the cylinder; and
    a sparge plate operable for aeration and pressurization wherein the combination of aeration, pressurization, and agitation will support microbial growth and metabolism at small scale and large scale with oxygen mass transfer rates at or above 150 mMoleOxygen/Liter/Hr when operating with sparge gas consisting of air only; and
    a containment bag, operable to contain material for one or more of microbial growth culturing microorganisms and recombinant protein production; and
    a heat transfer jacket operable for heating/cooling wherein the cylinder and first head further comprise an external heat transfer fluid cavity; and
    a heat transfer jacket operable for heating/cooling wherein the removable second head further comprise an external heat transfer fluid cavity.

2. The horizontal fermentor of claim 1, wherein the second head is removable from the second end of the vessel.

3. The horizontal fermentor of claim 1, wherein one or both of the first and second heads are dished shape.

4. The horizontal fermentor of claim 1, wherein the second head is closed using a quick release clamp.

5. The horizontal fermentor of claim 1, further comprising one or more of baffles disposed within said horizontal cylinder for agitation and mixing.

6. The horizontal fermentor of claim 1, further comprising one or more agitators, each operable to agitate and mix within the horizontal fermentor.

7. The horizontal fermentor of claim 5, wherein each of the one or more agitators comprises one or more impellers.

8. The horizontal fermentor of claim 5, wherein one or more of baffles comprising:
    one or more heating/cooling channels.

9. The horizontal fermentor of claim 1, wherein the fermentor is operable for one or more of microbial growth, culturing microorganisms and recombinant protein production.

10. The horizontal fermentor of claim 1, wherein the fermentor is operable for one or more sterile inlet and one or more sterile outlet ports.

11. The horizontal fermentor of claim 1, wherein the sterile ports are operable for one or more additions or withdrawals of gas or liquid.

12. The horizontal fermentor of claim 1, wherein the containment bag is a single use disposable containment bag.

13. The horizontal fermentor of claim 10, wherein the single use bag inclusive of internal mixing components are pre-sterilized prior to use in production.

14. The horizontal fermentor of claim 10, wherein the containment bag is operable to be sealed when containing the material.

15. The horizontal fermentor of claim 10, wherein the horizontal fermentor single use containment bag is operable to hold an internal pressure of greater than atmospheric.

16. The horizontal fermentor of claim 1, wherein the horizontal fermentor is operable to hold an internal pressure of greater than atmospheric.

17. The horizontal fermentor of claim 1, wherein the horizontal configuration results in a low profile at large scale whereby fermentors can be deployed in facilities with limited ceiling height.

18. A modular horizontal fermentor for production of microbes comprising:
    a two horizontal cylindrical modules oriented so that the axis of each cylindrical module is horizontal, wherein the two horizontal cylindrical modules comprises a left-most cylindrical module and a right-most cylindrical module, the left-most cylindrical module having a right end joined to a left end of the right-most cylindrical module;
    a first head affixed to and sealing a left end of the left-most cylindrical module; and
    a second head affixed to a right end of the right-most cylindrical module, the second head operable to open allowing access to the interior of horizontal fermentor and operable to close sealing the right end of the right-most cylinder and wherein said cylindrical module comprises a first head affixed to and sealing the first end of the cylinder; and a second head affixed to a second end of the cylinder, the second head operable to open allowing access to the interior of the cylinder and operable to close thereby sealing the second end of the cylinder and a heat transfer jacket operable for heating/cooling wherein the cylinder and first head further comprise an external heat transfer fluid cavity and a heat transfer jacket operable for heating/cooling wherein the removable second head further comprise an external heat transfer fluid cavity.

19. The modular horizontal fermentor of claim 18, wherein incremental batch volume size is increased by cylindrical modular expansion while maintaining constant input power per unit volume.

20. The modular horizontal fermentor of claim 18, wherein intermediate cylindrical modules comprise an external heat transfer jacket for heating/cooling.

21. The modular horizontal fermentor of claim 18, wherein intermediate cylindrical module further comprise one or more of baffles comprising:
   one or more heating/cooling channels.

22. A modular horizontal fermentor for production of microbes comprising:
   a plurality of horizontal cylindrical modules oriented so that the axis of each cylindrical module is horizontal, wherein the plurality of horizontal cylindrical modules comprises a left-most cylindrical module, one or more central cylindrical modules and a right-most cylindrical module, the left-most cylindrical module having a right end joined to a left end of one of the central cylindrical module, the right-most cylindrical module having a left end joined to a right end of one of the central cylindrical modules;
   a first head affixed to and sealing a left end of the left-most cylindrical module; and
   a second head affixed to a right end of the right-most cylindrical module, the second head operable to open allowing access to the interior of horizontal fermentor and operable to close sealing the right end of the right-most cylinder and wherein said cylindrical module further comprises a first head affixed to and sealing the first end of the cylinder; and a second head affixed to a second end of the last cylinder, the second head operable to open allowing access to the interior of the cylinder and operable to close thereby sealing the second end of the cylinder and a heat transfer jacket operable for heating/cooling wherein the cylinder and first head further comprise an external heat transfer fluid cavity and a heat transfer jacket operable for heating/cooling wherein the removable second head further comprise an external heat transfer fluid cavity.

23. The modular horizontal fermentor of claim 22, wherein incremental batch volume size is increased by modular expansion while maintaining constant input power per unit volume.

24. The modular horizontal fermentor of claim 22, wherein one or more intermediate cylindrical modules comprise an external heat transfer jacket for heating/cooling.

25. The modular horizontal fermentor of claim 22, wherein one or more intermediate cylindrical module baffles further comprise one or more of baffles comprising:
   one or more heating/cooling channels.

* * * * *

UNITED STATES PATENT AND TRADEMARK OFFICE
CERTIFICATE OF CORRECTION

PATENT NO. : 9,683,208 B2  
APPLICATION NO. : 15/218136  
DATED : June 20, 2017  
INVENTOR(S) : Ernest L. Stadler Page 1 of 1

It is certified that error appears in the above-identified patent and that said Letters Patent is hereby corrected as shown below:

On the Title Page

Item (54) Title should read:  
--HORIZONTAL SINGLE USE PRESSURIZABLE MODULAR MULTI-AGITATOR MICROBIAL FERMENTOR--

Signed and Sealed this  
Third Day of October, 2017

Joseph Matal  
*Performing the Functions and Duties of the*  
*Under Secretary of Commerce for Intellectual Property and*  
*Director of the United States Patent and Trademark Office*